United States Patent
Niesmiejanow

(10) Patent No.: US 9,629,387 B2
(45) Date of Patent: Apr. 25, 2017

(54) METHOD FOR STERILIZATION AND HOMOGENIZATION OF LIQUID PRODUCTS

(71) Applicant: E.K.A.D Innotech Sp. z o.o., Gdańsk (PL)

(72) Inventor: Ewgienij Niesmiejanow, Kaliningrad (RU)

(73) Assignee: E.K.A.D. Innotech Sp. z o.o., Gdańsk (PL)

(*) Notice: Subject to any disclaimer, the term of this patent is extended or adjusted under 35 U.S.C. 154(b) by 16 days.

(21) Appl. No.: 14/432,017

(22) PCT Filed: Sep. 25, 2013

(86) PCT No.: PCT/IB2013/058853
§ 371 (c)(1),
(2) Date: Mar. 27, 2015

(87) PCT Pub. No.: WO2014/049538
PCT Pub. Date: Apr. 3, 2014

(65) Prior Publication Data
US 2015/0237909 A1 Aug. 27, 2015

(30) Foreign Application Priority Data
Sep. 28, 2012 (PL) .......................... 400960

(51) Int. Cl.
*A23L 3/015* (2006.01)
*A61L 2/02* (2006.01)
(Continued)

(52) U.S. Cl.
CPC .............. *A23L 3/0155* (2013.01); *A23C 3/00* (2013.01); *A23C 3/033* (2013.01); *A23C 3/04* (2013.01);
(Continued)

(58) Field of Classification Search
CPC .......... A23L 3/0155; A23L 3/015; A23L 2/42; A61L 2/02; A23C 3/00; A23C 3/033; A23C 3/04; A23C 2210/15; A23V 2002/00
See application file for complete search history.

(56) References Cited

U.S. PATENT DOCUMENTS 3,672,823 A * 6/1972 Boucher ................ A61L 2/025
134/1
5,466,425 A * 11/1995 Adams ...................... A61L 2/02
210/243
(Continued)

FOREIGN PATENT DOCUMENTS

RU 2166155 * 4/2001

OTHER PUBLICATIONS

English Translation for RU 2166155 published Apr. 2001.*
Search report for PCT/IB2013/05883, Jul. 4, 2014.
Written Opinion for PCTIB2013/058853, Jul. 4, 2014.

*Primary Examiner* — Anthony Weier
(74) *Attorney, Agent, or Firm* — Synthesis Intellectual Property LLC

(57) ABSTRACT

The method of the invention is characterized in that in the first phase the device installation is filled with processed liquid product, yielding a low pressure zone and then the processed liquid product is introduced under high pressure into the cavitation process, where moving at a rate of not less than 3 m/s and under pressure of not less than 20 bar is introduced to the cavitation and rotation location of the separated streams of the processed liquid product, which rotating in the further part, in the longitudinal axis of the cavitator, move in the opposite directions, resulting in differential pressure leading to cavitation process with effects characteristic for sterilization and homogenization with heterogeneous parameters, wherein in the next phase a separation takes place into a liquid product, which has a particle size larger than 600 nm and a liquid product which has a particle size smaller than 600 nm, wherein the liquid product of larger particle size is directed to cooling and complementary cavitation reprocessing, and the liquid product of smaller particle size is subjected to particle size analysis control, by which the liquid product, which meets the preset parameters, is directed to the finished product acceptance, (Continued)

and the liquid product which does not meet the acceptance criteria is sent to the next reprocessing.

4 Claims, 1 Drawing Sheet

(51) Int. Cl.
    *A23C 3/00*            (2006.01)
    *A23C 3/033*         (2006.01)
    *A23L 2/42*           (2006.01)
    *A23C 3/04*           (2006.01)

(52) U.S. Cl.
    CPC ................. *A23L 2/42* (2013.01); *A23L 3/015* (2013.01); *A61L 2/02* (2013.01); *A23C 2210/15* (2013.01); *A23V 2002/00* (2013.01)

(56) References Cited

U.S. PATENT DOCUMENTS

| | | | | |
|---|---|---|---|---|
| 5,611,993 A * | 3/1997 | Babaev | ................... | A61L 2/025 204/158.2 |
| 6,019,947 A * | 2/2000 | Kucherov | ................. | A61L 2/02 210/748.01 |
| 7,410,654 B2 * | 8/2008 | Koide | .................... | A61K 35/64 424/275.1 |
| 2006/0118495 A1 * | 6/2006 | Kondratalv | ............... | C02F 1/34 210/748.03 |
| 2008/0095661 A1 * | 4/2008 | Kohler | ...................... | A61L 9/20 422/20 |
| 2009/0127207 A1 * | 5/2009 | Okamoto | ................ | B63B 13/00 210/747.6 |
| 2009/0159461 A1 * | 6/2009 | McCutchen | ......... | B01D 9/0022 205/751 |
| 2010/0032354 A1 * | 2/2010 | Uematsu | ................ | B01F 3/0446 210/150 |

* cited by examiner

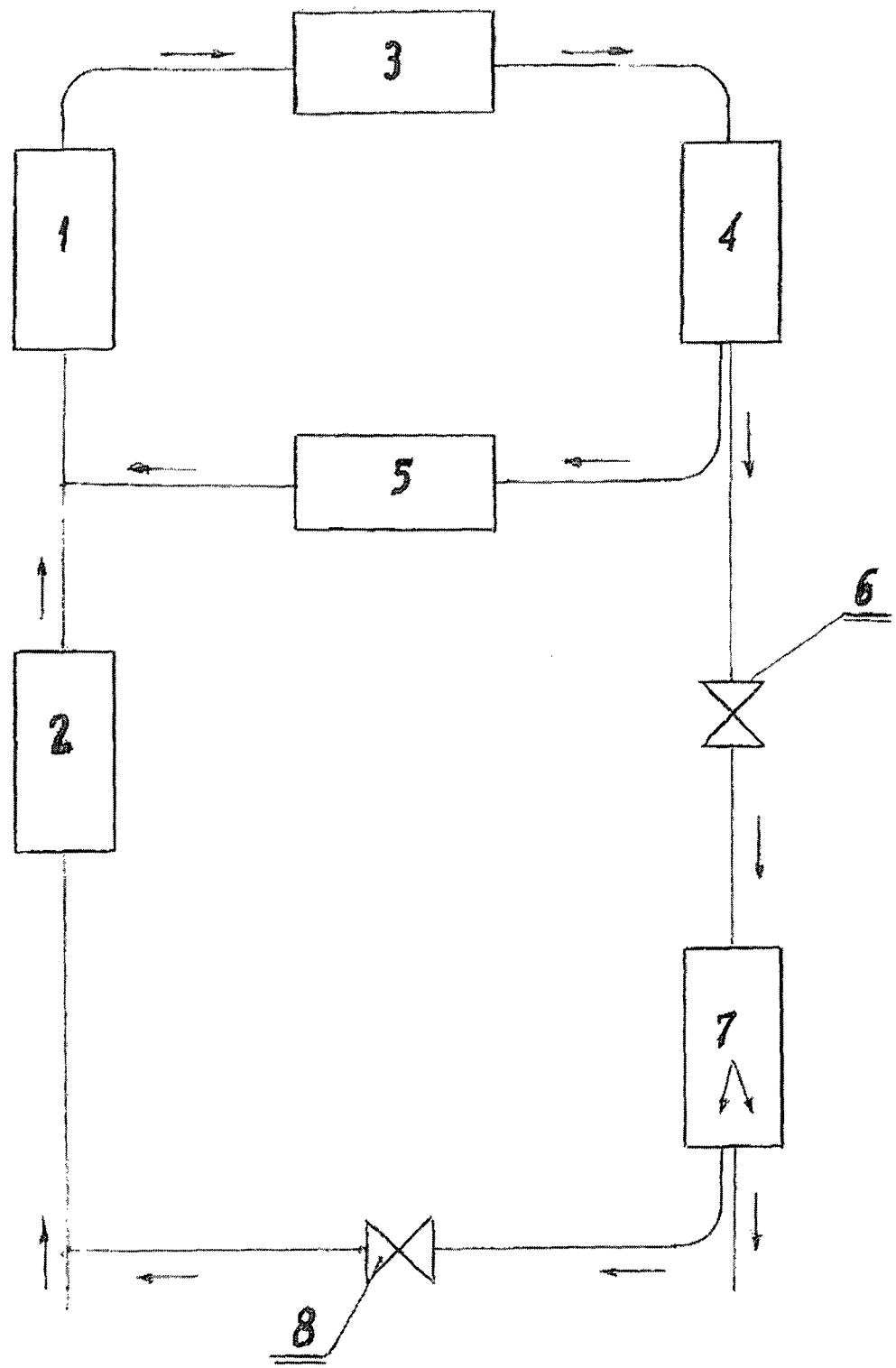

METHOD FOR STERILIZATION AND HOMOGENIZATION OF LIQUID PRODUCTS

CROSS-REFERENCE TO RELATED APPLICATIONS

This disclosure claims the benefit of priority to WIPO Patent Application No. WO/2014/049538, filed 25 Sep. 2013; which claims priority to PL Application No. 400960, filed 28 Sep. 2012; the disclosures of which are incorporated herein in their entirety.

FIELD OF THE INVENTION

A method and device for sterilization and homogenization of liquid products

BRIEF DESCRIPTION OF THE FIGURE

For a more complete understanding of the disclosure, reference should be made to the following detailed description and accompanying drawing FIGURE wherein:

FIG. 1 is a schematic representation of the herein described device.

While specific embodiments are illustrated in the FIGURE, with the understanding that the disclosure is intended to be illustrative, these embodiments are not intended to limit the invention described and illustrated herein.

DETAILED DESCRIPTION

The present invention provides a method and a device for sterilization and homogenization of liquid products, preferably liquid food products.

Patent application specification No. P.382264 discloses an embodiment of a device for cavitation processing of liquid media and a method of use of said device, consisting of a rotating disk mounted on a drive shaft, wherein the rotating disk is located between two fixed disks identical in their mirror image, which constitute, as intended, a tight housing for the device, wherein the fixed disks contain through holes and have working surfaces shaped in form of numerous concentric peripheral channels, and numerous radial channels that form peripheral sectorial projections on the fixed disc working surfaces. Both working surfaces of the rotating disk are shaped in the form of similar numerous concentric peripheral channels and radial channels that form similar sectorial projections on the rotating disk surfaces, also the working surface configuration of rotating disk and fixed disks cause the rotating disc sector projections to move in the peripheral channels of the fixed discs during the movement of the drive shaft, and moreover, each of the fixed discs is provided with at least one inlet port and at least one outlet port which is located in the collective annular channel formed by the fixed discs put together. Mode of operation of the device for cavitation processing of liquid media is characterized in that there is a forced flow of a heated liquid medium from the inlet port into the drive shaft chamber, then between the rotating disk and the fixed disk, to the annular channel and to its outflow port, during which sectorial projections of the rotating disk, cyclically open and close the flow in the flow channels formed by radial channels of the rotating disc and fixed discs creating conditions for cavitation phenomenon occurrence, wherein the cavitation microbubbles containing vapors of the heated liquid implode, releasing the heat to the environment, and the intensity of cavitation, understood as temperature increase of the liquid medium flowing through the device, is modified by varying the speed of the rotating disc and/or by varying the flow rate of the medium fed to the chamber.

The aim of the invention is to develop a method and a device for sterilization and homogenization of liquid products to obtain a significant reduction or the complete elimination of the bacteria contained within, and their spores, viruses, fungi and mold. The goal of the invention was accomplished according to the invention as a method and device for sterilization and homogenization of liquid products, in which in the embodiment of the method in the first phase the device installation is filled with processed liquid product, yielding a low pressure zone and then the processed liquid product is introduced under high pressure into the cavitation process, where moving at a rate of not less than 3 m/s and under pressure of not less than 20 bar is introduced to the cavitation and rotation location of the separated streams of the processed liquid product, which rotating in the further part, in the longitudinal axis of the cavitator, move in the opposite directions, resulting in differential pressure leading to the cavitation process with effects characteristic for sterilization and homogenization with heterogeneous parameters, wherein in the next phase separation takes place into a liquid product, which has a particle size larger than 600 Nm, and a liquid product which has a particle size smaller than 600 Nm, wherein the liquid product of larger particle size is directed to cooling and complementary cavitation reprocessing, and the liquid product of smaller particle size is subjected to particle size analysis control, by which the liquid product, which meets the preset parameters, is directed to the finished product acceptance, and the liquid product that does not meet the acceptance criteria is sent to the next reprocessing. The device of the invention comprises a low pressure pump which is used for filling the device installation with processed liquid product, wherein in a subsequent operation particle size analyzer switches the high pressure pump on, introducing at a pressure not less than 20 bar the processed liquid product to the cavitator, where cavitation process takes place, wherein the resulting liquid product having a heterogeneous structure is introduced into the separator centrifuge in which, depending on the parameters, the separation takes place to a flow into the heat exchanger and cavitation reprocessing and a flow through the valve to the particle size analyzer, which directs the final liquid product to the reception point.

In the embodiment of the invention, the cavitation process belongs to the leading ones because it causes cavitation process regulation of the interaction area on the processed product, by varying the characteristic flow parameters such as pressure, illustrating the cavitation effect. An important advantage of the method is production of products with improved organoleptic qualities, and also containing a significantly reduced number of all kinds of bacteria and spores, fungi and mold. An important performance advantage is also a significantly extended shelf life and range of storage conditions of the processed products.

The object of the invention is shown in the embodiment in a drawing depicting schematically the device construction in the form of a block diagram.

The device for sterilization and homogenization of liquid products comprises a low pressure pump 2 and a high pressure pump 1 pumping the liquid product for processing in the cavitator 3. In another operation, the processed liquid product is subjected to a separator centrifuge operation 4, and then moves as two streams to the heat exchanger 5 or the valve 6 and to the particle size analyzer 7, as well as, in the unforeseen situations, to the emergency valve 8 when it is necessary to solve the existing emergency problems.

The embodiment of the invention has been described in a more detailed way on milk processing.

Example

After filling the device installation with milk in the low pressure zone, after the activation of the particle size analyzer 7, the milk is introduced under high pressure to cavitator 3 for cavitation processing, wherein moving at a rate of 3 m/s and under pressure of 10 bar is introduced to the cavitation and rotation location of the separated streams of milk, which rotate in the further part, in the longitudinal axis of the cavitator, and move in the opposite directions, resulting in differential pressure leading to the cavitation process with effects of sterilization and homogenization with heterogeneous parameters, wherein in the next phase milk separation takes place into that one, which has larger particle size, wherein the processed liquid product, milk for example, moves at a rate of 3 m/s under pressure of 10 bar is directed to cavitation and rotation location of the separated streams of milk which rotating in the further part, in the longitudinal axis of the cavitator, move in the opposite directions, resulting in differential pressure leading to cavitation process with effects of sterilization and homogenization with heterogeneous parameters, wherein in the next phase milk separation takes place, into milk which has a particle size larger than 600 Nm, and milk which has a particle size smaller than 600 Nm. Milk of larger particles is directed to cooling in a heat exchanger 5, and the milk of smaller particle size is subjected to control in particle size analyzer 7, whereby the milk, which meets the preset parameters is directed to the finished product acceptance. In such a way homogenized and sterilized milk is obtained.

What is claimed:

1. A method of processing liquid products, comprising:
   introducing a processed liquid product as two rotating countercurrent streams into a cavitator at a velocity of not less than 3 m/s and at a pressure of not less than 20 bar;
   forming a differential pressure within the cavitator which effects sterilization and homogenization of the liquid product;
   separating an outflow from the cavitator into a first liquid product which has a particle size smaller than 600 nm, and a second liquid product which has a particle size greater than 600 nm;
   reprocessing the second liquid product by adding the second liquid product to the processed liquid product; and
   particle size analyzing the first liquid product.

2. The method of claim 1, wherein reprocessing the second liquid product includes cooling the second liquid product in a heat exchanger, and then introducing the cooled second liquid product into the cavitator.

3. The method of claim 1, wherein particle size analysis of the first liquid product based on preset parameters affects the direction of the first liquid product to reprocessing or product acceptance.

4. A method of processing liquid products, comprising:
   introducing a processed liquid product as two rotating countercurrent streams into a cavitator at a velocity of not less than 3 m/s and at a pressure of not less than 20 bar;
   forming a differential pressure within the cavitator which effects sterilization and homogenization of the liquid product;
   separating an outflow from the cavitator into a first liquid product which has a particle size smaller than 600 nm, and a second liquid product which has a particle size greater than 600 nm;
   reprocessing the second liquid product; and
   particle size analyzing the first liquid product, wherein reprocessing the second liquid product includes cooling the second liquid product in a heat exchanger, and then introducing the cooled second liquid product into the cavitator.

* * * * *